US010376925B2

(12) United States Patent
Mingyan

(10) Patent No.: US 10,376,925 B2
(45) Date of Patent: Aug. 13, 2019

(54) AUTOMATED SILKWORM SEX SORTING

(71) Applicant: China Jiliang University, Zhejiang (CN)

(72) Inventor: Zhao Mingyan, Zhejiang (CN)

(73) Assignee: China Jiliang University, Zhejiang (CN)

( * ) Notice: Subject to any disclaimer, the term of this patent is extended or adjusted under 35 U.S.C. 154(b) by 0 days.

(21) Appl. No.: 15/967,985

(22) Filed: May 1, 2018

(65) Prior Publication Data

US 2018/0318883 A1    Nov. 8, 2018

(30) Foreign Application Priority Data

May 8, 2017   (CN) ............................ 2017 1 0331957

(51) Int. Cl.
- *B07C 5/342* (2006.01)
- *B07C 5/02* (2006.01)
- *B07C 5/38* (2006.01)
- *A01K 67/04* (2006.01)

(52) U.S. Cl.
CPC ............ *B07C 5/3422* (2013.01); *A01K 67/04* (2013.01); *B07C 5/02* (2013.01); *B07C 5/38* (2013.01)

(58) Field of Classification Search
CPC ......... B07C 5/02; B07C 5/342; B07C 5/3422; B07C 5/362; B07C 5/38; A01K 67/04
See application file for complete search history.

(56) References Cited

U.S. PATENT DOCUMENTS

| | | | | |
|---|---|---|---|---|
| 3,206,022 A * | 9/1965 | Roberts, Jr. | ............. | B07C 5/342 209/582 |
| 4,246,098 A * | 1/1981 | Conway | ................ | B07C 5/3422 209/558 |
| 7,737,379 B2 * | 6/2010 | Witdouck | ............... | B07C 5/342 209/588 |
| 8,025,027 B1 * | 9/2011 | Morales-Ramos | ........................ | A01K 67/033 119/6.5 |
| 8,755,571 B2 * | 6/2014 | Tsai | .......................... | G06K 9/00 382/110 |
| 9,676,004 B2 * | 6/2017 | Cohn | ..................... | B07C 5/3425 |
| 9,992,983 B1 * | 6/2018 | Sobecki | ..................... | B07B 1/55 |
| 2015/0008163 A1 * | 1/2015 | Nimmo | ................ | A01K 67/033 209/17 |
| 2018/0121764 A1 * | 5/2018 | Zha | ......................... | G06T 7/0004 |
| 2018/0318884 A1 * | 11/2018 | Mingyan | ................ | B07C 5/3422 |
| 2018/0369867 A1 * | 12/2018 | Sobecki | ..................... | B07B 1/46 |

FOREIGN PATENT DOCUMENTS

| | | | | |
|---|---|---|---|---|
| CN | 106198448 A | * | 12/2016 | ............... B07C 5/02 |
| WO | WO-2017158216 A1 | * | 9/2017 | ............ A01M 1/026 |

OTHER PUBLICATIONS

English Translation of CN 106198448 A; Yang et al.; Dec. 2016.*

* cited by examiner

*Primary Examiner* — Joseph C Rodriguez
(74) *Attorney, Agent, or Firm* — Kunzler Bean & Adamson

(57) ABSTRACT

For sorting silkworm chrysalises, a feed mechanism positions silkworm chrysalises on a delivery mechanism. The delivery mechanism receives and carries the silkworm chrysalises from the feed mechanism. A detection mechanism detects a female silkworm chrysalis based on an optical wavelength emitted by the female silkworm chrysalis. A sorting mechanism that sorts the silkworm chrysalises, putting female silkworm chrysalises into a female collecting box, and male silkworm chrysalises into male collecting box.

16 Claims, 3 Drawing Sheets

AUTOMATED SILKWORM SEX SORTING

CROSS-REFERENCE TO RELATED APPLICATIONS

This patent application claims priority to Chinese Patent Application No. 201710331957.8 filed on May 8, 2017 for China Jiliang University, Applicant and Zhao Mingyan, inventor, the entire contents of which are incorporated herein by reference for all purposes.

BACKGROUND INFORMATION

The subject matter disclosed herein relates to silkworm chrysalises sorting.

BRIEF DESCRIPTION

An apparatus for automatically sorting silkworm chrysalises by sex is disclosed. The apparatus includes:

a feed mechanism that positions silkworm chrysalises waiting to be sorted;

a delivery mechanism that carries chrysalises coming from the feed mechanism to a dark room;

a detection mechanism that is disposed in the upper place of the dark room and that is located on the route of the delivery mechanism, wherein detection mechanism takes pictures of silkworm chrysalises and detects the silkworm chrysalis sex;

a sorting mechanism that sorts the silkworm chrysalises according to the results from the detection mechanism, putting female chrysalises into a female collecting box, and male chrysalises into a male collecting box.

The apparatus is high-efficiency and high-accuracy.

DETAILED DESCRIPTION

Figure 1:
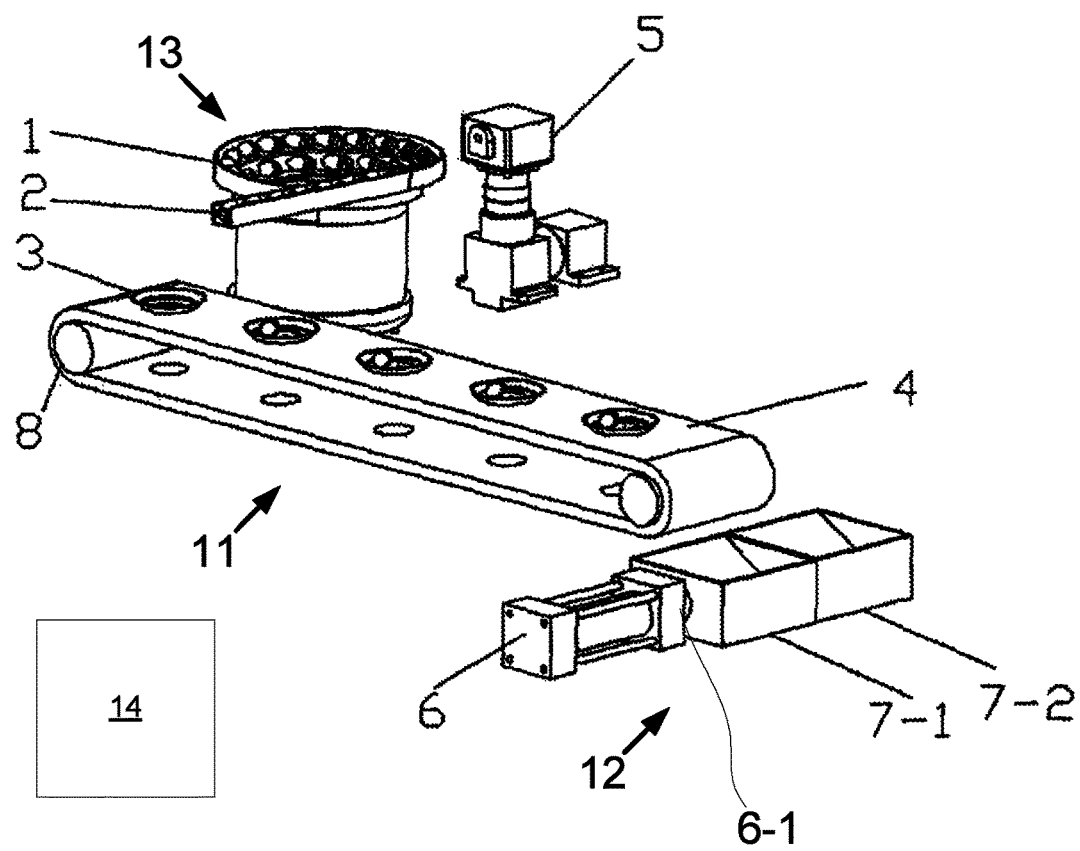
FIG. 1 is a perspective drawing illustrating one embodiment of a silkworm chrysalis sex sorting apparatus.

Female and male silkworm chrysalises should be breed in pairs or there will be a waste. However, breeding in pairs requires sorting by sex. Thus far, in the production of silkworm chrysalises, manpower is needed to finish cutting silkworm cocoons and sexing silkworm chrysalises. This production needs lots of manpower, and the efficiency is poor. As silkworm chrysalises need to be finished in 5 to 10 days, large work force is needed in a short time. For example, Shandong Guatong enterprise, the largest silkworm eggs producer in China, must hire around 1000 people temporarily. The number of skilled workers is getting lower every year, while the cost of work force is getting higher, the cost of every piece of cocooning frame is ¥30, the cost of temporary worker is ¥7 to ¥8 (taking up around 26% of the total expense). Sexing silkworm chrysalises not only needs good eyesight, but also needs certain skills and proficiency. The major problem the largest silkworm eggs producers face is that sexing silkworm chrysalises needs much manpower, and the time is limited, while skillful workers cannot meet the needs. At the same time, the accuracy of sexing silkworm chrysalises is directly related to silkworm eggs' quality and purity of their breeds. According to data provided by the Zhejiang silkworm quality quarantine inspection station concerning the average hybrid rate 80 to 100 times per year from 2005 to 2016, considerable decline exists, falling from the highest 99.66% to the lowest 98.65%. The decline of the hybrid rate will directly influence the quality of silkworm eggs, the production of silkworm chrysalises and the quality of silk.

From this, there are still problems existing like low-speed and low accuracy with machine sorting according to silkworm chrysalises' mass and size, or with skillful workers sexing to silkworm chrysalises. In China, the need for high quality silkworm eggs is large, so sorting methods with high-speed and high-accuracy are desperately needed, while with today's technology, these needs cannot be satisfied. Using the genetic techniques and gene editing techniques, female silkworm chrysalises can release orange fluorescence all in their life span, with this characteristic, those technical problems can be solved. To deal with the problems that factories are facing, a new silkworm breed needs to be incubated which has advantages like being easy to sex and easy to produce to reduce the cost and increase the quality of silkworm eggs and production efficiency of enterprises. Therefore, the embodiments use the difference between female and male silkworm chrysalises' characteristics to build a system which can sex silkworm chrysalises with high-speed, high accuracy.

The embodiments provide a fully-automatic machine for sexing silkworm chrysalises with high efficiency and high accuracy to solve the problems of current technology that requires lots of manpower and has low sexing accuracy. The embodiments disclose a solution for automatically sexing silkworm chrysalises. Based on the full-automatic sorting machine for sexing silkworm chrysalises, it includes the following components:

Feed mechanism: make silkworm chrysalises waiting to be sorted sit on corresponding positions.

Delivery mechanism: multiple positions are set to carry silkworm chrysalises coming from the feed mechanism, and feed mechanism delivery these silkworm chrysalises as mentioned.

Detection mechanism: sitting in the upper place of the dark room, which is located on the route of the delivery mechanism, the detection mechanism takes pictures of silkworm chrysalises waiting to be sorted and runs programs to detect their sex, when silkworm chrysalises are sent into the dark room by the delivery mechanism.

Sorting mechanism: according to the results coming from the detection mechanism, sorting mechanism sort silkworm chrysalises, putting female ones into female collecting box, and male ones into male collecting box.

Optional, the feed mechanism as mentioned has a vibrating plate. When silkworm chrysalises as mentioned are put into the vibrating plate, they will be transferred to corresponding positions on by one by the delivery mechanism.

Optional, the delivery mechanism as mentioned includes a conveyor belt and pneumatic devices. The conveyor belt has spacing holes sitting on its surface as working positions, and lies beneath the delivery mechanism, so does the pneumatic devices.

In one embodiment, the detection mechanism has a CCD camera capable of fluorescence detection. The CCD camera distinguishes silkworm chrysalises by sex through machine vision, wherein the orange ones are females, while the others are males. And the results are sent to sort mechanism, and then sort mechanism sorts and collects these silkworm chrysalises.

In one embodiment, the sort mechanism includes a female collecting box, a male collecting box, and a driving mechanism. The output shaft of the driving mechanism may be connected to collecting boxes. When the female one is falling, the driving mechanism drives the female collecting box to collect it. When the male one is falling, so drives the male collecting box to collect it.

In one embodiment, an illuminant is disposed near the CCD camera. During the process of fluorescence detection, once silkworm chrysalises are under the 554 nm light, the fluorescent protein in female ones will release 586 nm light. The CCD camera can detect the fluorescent protein when implementing a cutoff fluorescent filter whose central wavelength is 586 nm. The optical design of this mechanism is that using CREE CXA2530, high power LED bubbles implementing with 554 central wavelength cutoff fluorescent filters, the filters are used to keep the purity of the illuminant. When light hits on the dichroic mirror, it is reflected to the silkworm chrysalis, and CCD camera detects the silkworm chrysalis through dichroic mirror.

In one embodiment, pictures are taken by the CCD camera, and analyzed by image processing algorithm to separate silkworm chrysalises by sex. With the MYSQL database being built, silkworm chrysalises can be sorted by sorting mechanism under the control of single chip.

In one embodiment, in the spacing hole includes a taper cup, an elastic cushion, and a plug boss. The elastic cushion may be disposed on the bottom of the taper cup. Between the elastic cushion and the conveyor belt there are small holes and space which can be used as air channels. The plug boss may be disposed beneath the elastic cushion. The airflow goes into the air channels through the air tubes on the plug boss.

The following is a detailed description of the embodiments, but the present invention is not limited to these embodiments. The present invention covers any substitution, modification, equivalent method and scheme for the spirit and scope of the invention. In order to make public the invention, a thorough, detailed description with examples of the specific details is provided.

Refer to the attached Figures in the following paragraphs for a more specific description of the invention. It should be noted that the attached drawings are both in a simplified form and use non-precise proportions, which are only used to facilitate and clarify the purpose of the embodiment of the invention.

Figure 2:
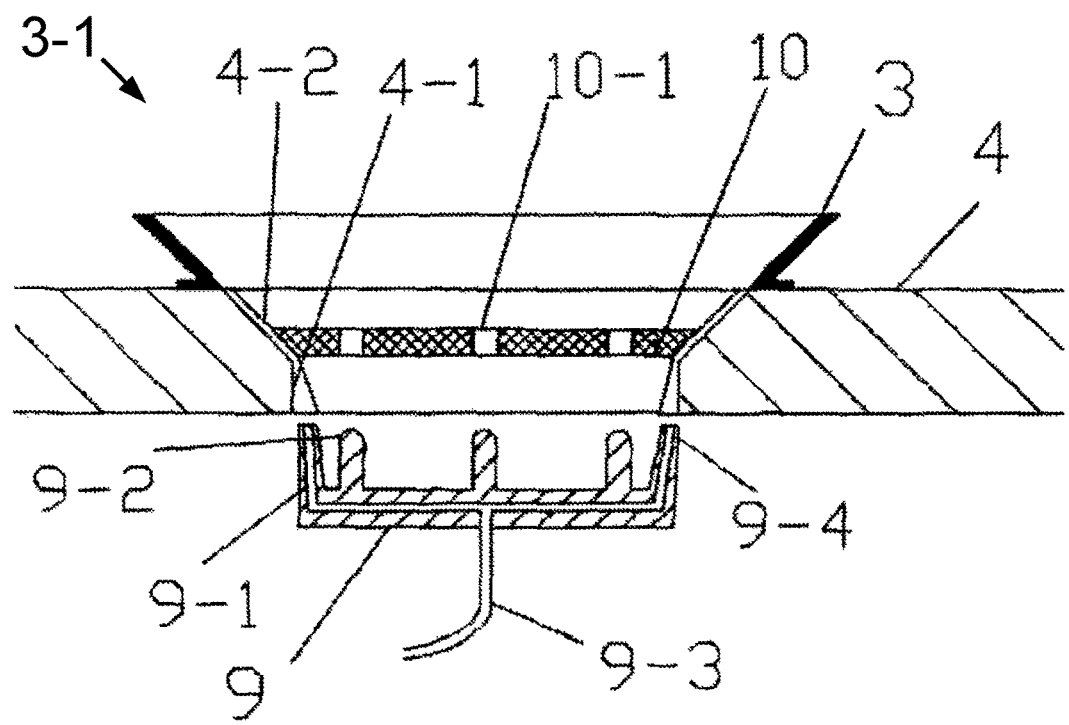
FIG. 2 is a side view drawing illustrating one embodiment of the silkworm chrysalis sex sorting apparatus.
Figure 3:
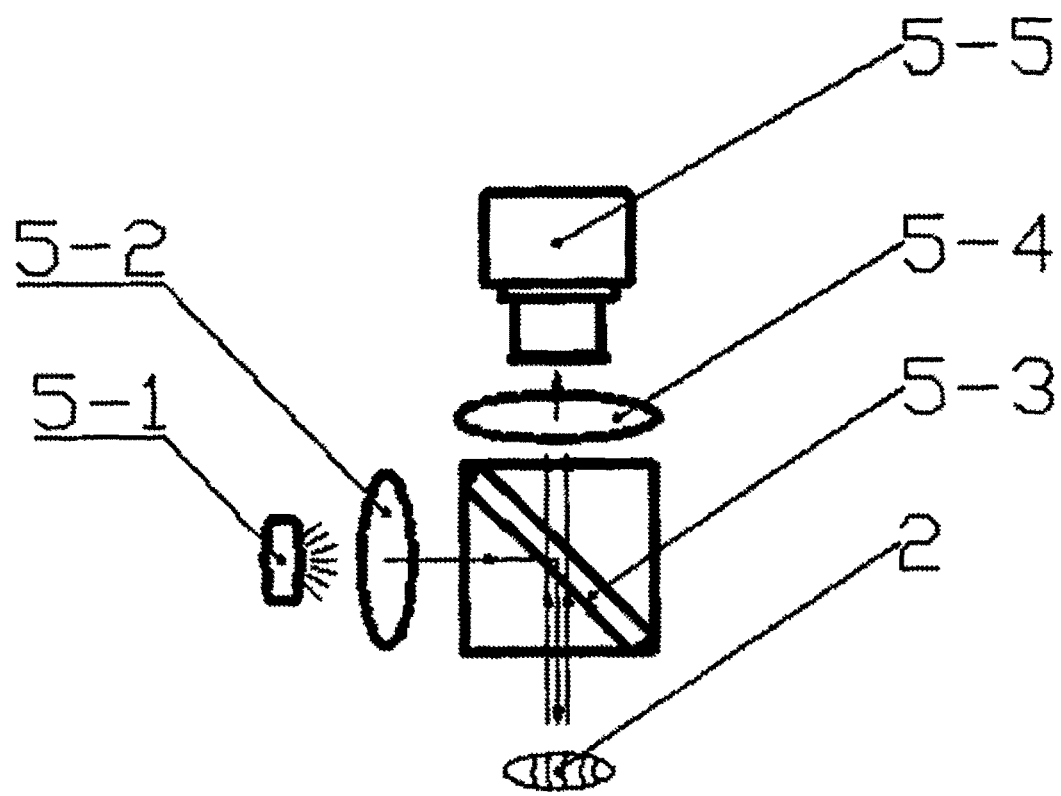
FIG. 3 is a side view drawing illustrating one embodiment of a detection mechanism.

FIGS. 1-3 include a feed mechanism 13, silkworm chrysalis 2, taper cups 3, a conveyor belt 4, a taphole 4-1, air channels 4-2 of the conveyor belt 4, a detection mechanism 5, a light emitting diode (LED) 5-1, a green fluorescence filter 5-2, a dichroic mirror 5-3, orange fluorescence filter 5-4, a charge-coupled device (CCD) camera 5-5 for fluorescence detection, a driving mechanism 6, a female collecting box 7-1 a male collecting box 7-2, a synchronous belt wheel 8, a plug boss 9, air channels 9-1 of the plug boss 9, sensors 9-2, air tubes 9-3, a plug 9-4 of the taper cup 3, an elastic cushion 10, and elastic cushion holes 10-1.

FIG. 1 shows: the structure of a fully automatic apparatus and system for sorting silkworm chrysalises by sex, including the feed mechanism 13, the delivery mechanism 11, the detection mechanism 5, and the sorting mechanism 12. The feed mechanism 13 positions silkworm chrysalises 2 waiting to be sorted. The delivery mechanism 11 carries silkworm chrysalises 2 coming from the feed mechanism 13 to a dark room (not shown). The detection mechanism 5 may be disposed in an upper place of the dark room and located on the route of the delivery mechanism 11. The detection mechanism 5 takes pictures of silkworm chrysalises 2 waiting to be sorted and detects silkworm chrysalises' sex. The sorting mechanism 12 sorts the silkworm chrysalises 2 according to the results from the detection mechanism 5, putting female chrysalises 2 into the female collecting box 7-1, and male chrysalises 2 into the male collecting box 7-2.

The feed mechanism 13 may have a vibrating plate 1. When silkworm chrysalises 2 are put into the vibrating plate 1, the silkworm chrysalises 2 may be separated and transferred one by one to corresponding working positions 3-1 in a taper cup 3 of the conveyor belt 4 of the delivery mechanism 11. The delivery mechanism 11 includes the conveyor belt 4 with air channels 4-2. The conveyor belt 4 may comprise tapholes 4-1 with taper cups 3 at the working positions. The conveyor belt may pass beneath the detection mechanism 5, as do the air channels 4-2 of the conveyor belt 4, the air channels 9-1 of the plug boss 9, and the air tubes 0-3, referred to hereafter as the pneumatic devices.

The detection mechanism 5 may include a CCD camera 5-5. The CCD camera 5-5 is capable of fluorescence detection. The CCD camera 5-5 may distinguish the sex of silkworm chrysalises 2 through machine vision. In one embodiment, the orange silkworm chrysalises 2 are females, while the other silkworm chrysalises 2 are males. The results are sent to sorting mechanism 12, which sorts and collects the silkworm chrysalises 2.

The sorting mechanism 12 may include a female collecting box 7-1, a male collecting box 7-2, and a driving mechanism 6. In the depicted embodiment, the driving mechanism 6 is an air cylinder. An output shaft 6-1 of the driving mechanism 6 may be connected to the female collecting box 7-1 and the male collecting 7-2 box. When the female silkworm chrysalises 2 is falling from the conveyor belt 4, the driving mechanism 6 drives the female collecting box to collect the female silkworm chrysalises 2. When the male silkworm chrysalises 2 is falling from the conveyor belt 4, the driving mechanism 6 drives the male collecting box 7-2 to collect the male silkworm chrysalises.

When the vibrating plate 1 vibrates, silkworm chrysalises 2 waiting to be sorted fall into the taper cup 3 one by one. The vibration rate corresponds to the speed of the conveyor belt 4. The vibration rate and the speed are set to make sure that there is only one silkworm chrysalis 2 falling into each taper cup 3. Through adjusting the vibration rate and amplitude, the feed speed can be accurately controlled. Once the feed speed is adjusted, one and only one silkworm chrysalis 2 will fall into the taper cup 3.

After silkworm chrysalises 2 enter into the taper cups 3, the detection mechanism 5, detects the female silkworm chrysalises 2 and sends the results to a controller 14 which may direct the air cylinder driving mechanism 6 to move, so that female silkworm chrysalises 2 fall off of the conveyor belt 4 into the female collecting box 7-1, while male silkworm chrysalises 2 fall off the conveyor belt 4 into the male collecting box 7-2.

As shown in FIG. 2, taper cups 3 are set on the conveyor belt 4 at working positions 3-1. An elastic cushion 10 may be disposed at a bottom of the taper cup 3. The elastic cushion 10 may prevent mechanical and/or physical injury to the silkworm chrysalis 2. The elastic cushion 10 may be round. The diameter of the elastic cushion 10 may correspond to the length of average silkworm chrysalis 2. A plurality of elastic cushion holes 10-1, such as twelve elastic cushion holes 10-1, may be disposed in the elastic cushion 10.

Air channels 4-2 may be disposed surrounding the elastic cushion 10 on the conveyor belt 4, so that air flows are formed along the wall of the taper cup 3. The air flows may prevent the silkworm chrysalises 2 from falling with mechanical and/or physical injury. In addition, the air flows may position the silkworm chrysalis 2 to sit in the middle of the elastic cushion 10, so that it will be convenient to run the detection.

The plug boss 9 may include air channels 9-1 and a plug 9-4 supplied with air flow by the air tubes 9-3. When the plug boss 9 is inserted into the taphole 4-1, a tapered airflow is formed from the air channels 4-2 and from the elastic cushion holes 10-1. Sensors 9-2 set on the plug boss 9 may detect whether there is a silkworm chrysalis 2 on the elastic cushion 10.

FIG. 3 shows the detection mechanism 5. A female silkworm chrysalis 2 may express orange fluorescence throughout the chrysalis life cycle. After the light from the LED 5-1 goes through the green fluorescence filter 5-2, a green light with a 554 nm central wave length and 30 nm bandwidth is produced. The green light may strike the dichroic mirror 5-3 and refract on to the silkworm chrysalis 2. Under the green light, if the silkworm chrysalis 2 is female, the silkworm chrysalis 2 will release a light of 586 nm central length. The orange fluorescence filter 5-4 has 586 nm central length, and 20 nm band width, which can rule out interruption from other wave-length light, so that only light with 576 nm wave length to 596 nm wave length is passed. The CCD camera 5-5 for fluorescence detection detects the light with 586 nm wave length to identify the sex of the silkworm chrysalis. Therefore, fast detection of sex of silkworm chrysalises 2 can be achieved using machine vision recognition technology and lighting filters and other devices.

Images are taken by the CCD camera 5-5, and the images from the CCD camera 5-5 are analyzed by image processing algorithm of the controller 14 to separate silkworm chrysalises by sex. The image processing algorithm may employ a database to sort silkworm chrysalises 2 under the control of the controller 14 or a single chip.

The elements of the embodiments may be practiced separately or together in various combinations. The embodiments above do not constitute a limitation on the scope of protection of the technical scheme. Any modifications, equivalents and improvements made in the spirit and principles of the above implementation shall be included in the protection of the technical scheme.

The embodiments take advantage of a bioluminescent protein inserted into the female silkworm chrysalises 2. Using the biological fluorescent protein technology and machine vision technology, the embodiments sort the silkworm chrysalises 2 by sex. After the filters 5-2/5-4 with certain wave length are set on the illuminant, allowing the CCD camera 5-5 to filter out interference from other light, detection with high speed and accuracy can be achieved. Holes and taper cups 3 are set on the conveyor belt 4, so that the taper cup 3 with tapered airflow can be formed, and the physical damage to silkworm chrysalises 2 can be avoided. The embodiments have high efficiency and high accuracy sorting silkworm chrysalises 2 by sex.

What is claimed is:

1. An apparatus comprising:
    a feed mechanism that positions silkworm chrysalises on a delivery mechanism;
    the delivery mechanism comprising a plurality of positions that receives and carries the silkworm chrysalises from the feed mechanism;
    a detection mechanism comprising a charge-coupled device (CCD) camera, a light emitting diode (LED), a green fluorescence filter, and a dichroic mirror that detects a female silkworm chrysalis based on an optical wavelength emitted by the female silkworm chrysalis, wherein light from the LED goes through the green fluorescence filter producing a green light with a 554 nanometer (nm) central wave length and 30 nm bandwidth that is refracted by the dichroic mirror on the silkworm chrysalis, and wherein light from the silkworm chrysalis is transmitted through the dichroic mirror passing through an orange fluorescence filter with a 586 nm central wave length and a 20 nm bandwidth to the CCD camera; and
    a sorting mechanism that sorts the silkworm chrysalises, putting female silkworm chrysalises into a female collecting box, and male silkworm chrysalises into male collecting box.

2. The apparatus of claim 1, wherein the feed mechanism comprises a vibrating plate 1, wherein the silkworm chrysalises are put into the vibrating plate 1, the silkworm chrysalises transferred one by one to corresponding working positions on the delivery mechanism.

3. The apparatus of claim 2, wherein the delivery mechanism comprises a conveyor belt, the conveyor belt comprising tapholes with taper cups at the working positions.

4. The apparatus of claim 3, wherein the taper cups each comprise an elastic cushion and a plug boss, wherein the elastic cushion is disposed at the bottom of the taper cup, air channels are disposed between the elastic cushion and the conveyor belt, and the plug boss is disposed beneath the elastic cushion, the plug boss comprising air tubes and a plug that supply air flow to the air channels.

5. The apparatus of claim 1, wherein the green light stimulates the female silkworm chrysalis to emit an orange 586 nm light, which is transmitted through the dichroic mirror and the orange fluorescence filter and detected by the CCD camera to identify the female silkworm chrysalis.

6. The apparatus of claim 5, wherein images from the CCD camera are analyzed by an image processing algorithm to separate the silkworm chrysalises by sex.

7. The apparatus of claim 6, wherein the image processing algorithm employs a database to sort silkworm chrysalises.

8. The apparatus of claim 1, wherein the sort mechanism comprises a female collecting box, a male collecting box, and a driving mechanism, and wherein in response to a female silkworm chrysalises falling from a conveyor belt, the driving mechanism drives the female collecting box to collect the female silkworm chrysalises and in response to the male silkworm chrysalises falling from the conveyor belt, the driving mechanism drives the male collecting box to collect the male silkworm chrysalises.

9. A system comprising:
    a feed mechanism that positions silkworm chrysalises on a delivery mechanism;
    the delivery mechanism comprising a plurality of positions that receives and carries the silkworm chrysalises from the feed mechanism;
    a detection mechanism comprising a charge-coupled device (CCD) camera, a light emitting diode (LED), a green fluorescence filter, and a dichroic mirror that detects a female silkworm chrysalis based on an optical wavelength emitted by the female silkworm chrysalis, wherein light from the LED goes through the green fluorescence filter producing a green light with a 554 nanometer (nm) central wave length and 30 nm bandwidth that is refracted by the dichroic mirror on the silkworm chrysalis, and wherein light from the silkworm chrysalis is transmitted through the dichroic mirror passing through an orange fluorescence filter with a 586 nm central wavelength and a 20 nm bandwidth to the CCD camera;

a sorting mechanism that sorts the silkworm chrysalises, putting female silkworm chrysalises into a female collecting box, and male silkworm chrysalises into male collecting box; and a controller that controls the feed mechanism, the delivery mechanism, the detection mechanism, and the sorting mechanism.

10. The system of claim 9, wherein the feed mechanism comprises a vibrating plate 1, wherein the silkworm chrysalises are put into the vibrating plate 1, the silkworm chrysalises transferred one by one to corresponding working positions on the delivery mechanism.

11. The system of claim 10, wherein the delivery mechanism comprises a conveyor belt, the conveyor belt comprising tapholes with taper cups at the working positions.

12. The system of claim 11, wherein the taper cups each comprise an elastic cushion and a plug boss, wherein the elastic cushion is disposed at the bottom of the taper cup, air channels are disposed between the elastic cushion and the conveyor belt, and the plug boss is disposed beneath the elastic cushion, the plug boss comprising air tubes and a plug that supply air flow to the air channels.

13. The system of claim 9, wherein the green light stimulates the female silkworm chrysalis to emit an orange 586 nm light, which is transmitted through the dichroic mirror and the orange fluorescence filter and detected by the CCD camera to identify the female silkworm chrysalis.

14. The system of claim 13, wherein images from the CCD camera are analyzed by an image processing algorithm to separate the silkworm chrysalises by sex.

15. The system of claim 14, wherein the image processing algorithm employs, a database to sort silkworm chrysalises.

16. The system of claim 15, wherein the sort mechanism comprises a female collecting box, a male collecting box, and a driving mechanism, and wherein in response to a female silkworm chrysalises falling from a conveyor belt, the driving mechanism drives the female collecting box to collect the female silkworm chrysalises and in response to the male silkworm chrysalises falling from the conveyor belt, the driving mechanism drives the male collecting box to collect the male silkworm chrysalises.

* * * * *